(12) United States Patent
Borodic (10) Patent No.: US 9,950,042 B2
(45) Date of Patent: Apr. 24, 2018

(54) EXTENDED LENGTH BOTULINUM TOXIN FORMULATION FOR HUMAN OR MAMMALIAN USE

(71) Applicant: Revance Therapeutics, Inc., Newark, CA (US)

(72) Inventor: Gary E. Borodic, Quincy, MA (US)

(73) Assignee: REVANCE THERAPEUTICS, INC., Newark, CA (US)

( * ) Notice: Subject to any disclaimer, the term of this patent is extended or adjusted under 35 U.S.C. 154(b) by 0 days.

(21) Appl. No.: 14/754,268

(22) Filed: Jun. 29, 2015

(65) Prior Publication Data

US 2015/0297684 A1 Oct. 22, 2015

Related U.S. Application Data

(62) Division of application No. 13/132,855, filed as application No. PCT/US2009/066891 on Dec. 4, 2009, now Pat. No. 9,066,851.

(Continued)

(51) Int. Cl.
*A61K 38/48* (2006.01)
*A61K 8/02* (2006.01)
(Continued)

(52) U.S. Cl.
CPC ............ *A61K 38/4833* (2013.01); *A61K 8/02* (2013.01); *A61K 8/24* (2013.01); *A61K 8/33* (2013.01);
(Continued)

(58) Field of Classification Search
CPC .................................................. A61K 38/4893
See application file for complete search history.

(56) References Cited

U.S. PATENT DOCUMENTS

| 4,845,042 A | 7/1989 | Newman et al. |
| 4,861,627 A | 8/1989 | Mathiowitz et al. |

(Continued)

FOREIGN PATENT DOCUMENTS

| CA | 2376193 | 5/2000 |
| CH | 396311 | 7/1962 |

(Continued)

OTHER PUBLICATIONS

International Search Report and Written Opinion for PCT/US2011/036872 dated Sep. 14, 2011.

(Continued)

*Primary Examiner* — Rosanne Kosson
(74) *Attorney, Agent, or Firm* — Kenneth H. Sonnenfeld; Nicole Fortuné; King & Spalding LLP (57) ABSTRACT

An extended duration pharmaceutical composition including a botulinum neurotoxin, an adhesive agent, and a stabilizing macromolecule is disclosed. The composition effectively has all the properties to cause chemodenervation through a facial muscle, or other muscle, that predecessor botulinum toxin preparations have had as well as agents which create a fibrotic adhesion on the under surface of facial muscles (or other muscles) to the facial bone (or other bones) so that the facial bone tethers the under surface of the facial muscle, thereby causing fibrosis to the underlying fat pad. The composition can be used to treat various disorders. Methods of modifying facial contour for functional or cosmetic purposes in a human patient are disclosed which involve injecting a therapeutically effective amount of the disclosed compositions. A method of quantifying the extended duration of the compositions is also disclosed.

17 Claims, 3 Drawing Sheets

Related U.S. Application Data (60) Provisional application No. 61/193,513, filed on Dec. 4, 2008.

(51) Int. Cl.

| | | |
|---|---|---|
| *A61K 8/24* | (2006.01) | |
| *A61K 8/33* | (2006.01) | |
| *A61K 8/55* | (2006.01) | |
| *A61K 8/64* | (2006.01) | |
| *A61K 8/65* | (2006.01) | |
| *A61K 8/81* | (2006.01) | |
| *A61K 9/00* | (2006.01) | |
| *A61K 9/08* | (2006.01) | |
| *A61K 47/08* | (2006.01) | |
| *A61K 47/10* | (2017.01) | |
| *A61K 47/24* | (2006.01) | |
| *A61K 47/32* | (2006.01) | |
| *A61K 47/42* | (2017.01) | |
| *A61Q 19/08* | (2006.01) | |
| *A61K 8/66* | (2006.01) | |

(52) U.S. Cl.
CPC ............... *A61K 8/553* (2013.01); *A61K 8/64* (2013.01); *A61K 8/65* (2013.01); *A61K 8/66* (2013.01); *A61K 8/8111* (2013.01); *A61K 8/8141* (2013.01); *A61K 9/0019* (2013.01); *A61K 9/08* (2013.01); *A61K 38/4893* (2013.01); *A61K 47/08* (2013.01); *A61K 47/10* (2013.01); *A61K 47/24* (2013.01); *A61K 47/32* (2013.01); *A61K 47/42* (2013.01); *A61Q 19/08* (2013.01); *A61K 2800/48* (2013.01); *A61K 2800/5922* (2013.01); *A61K 2800/91* (2013.01); *C12Y 304/21005* (2013.01); *C12Y 304/24069* (2013.01)

(56) References Cited

U.S. PATENT DOCUMENTS

| | | |
|---|---|---|
| 5,053,005 A | 10/1991 | Borodic |
| 5,069,936 A | 12/1991 | Yen et al. |
| 5,437,291 A | 8/1995 | Pasricha et al. |
| 5,512,547 A | 4/1996 | Johnson et al. |
| 5,562,906 A | 10/1996 | Amon |
| 5,562,907 A | 10/1996 | Amon |
| 5,576,468 A | 11/1996 | Lubowitz |
| 5,670,484 A | 9/1997 | Binder |
| 5,696,077 A | 12/1997 | Johnson et al. |
| 5,714,468 A | 2/1998 | Binder |
| 5,721,215 A | 2/1998 | Barnabas et al. |
| 5,756,468 A | 5/1998 | Johnson et al. |
| 5,766,176 A | 6/1998 | Duncan |
| 5,846,929 A | 12/1998 | Johnson et al. |
| 5,939,070 A | 8/1999 | Johnson et al. |
| 5,989,545 A | 11/1999 | Foster et al. |
| 6,051,239 A | 4/2000 | Simpson et al. |
| 6,087,327 A | 7/2000 | Pearce et al. |
| 6,100,306 A | 8/2000 | Li et al. |
| 6,203,794 B1 | 3/2001 | Dolly et al. |
| 6,210,707 B1 | 4/2001 | Papahadjopoulos et al. |
| 6,214,602 B1 | 4/2001 | Johnson et al. |
| 6,221,075 B1 | 4/2001 | Tormala et al. |
| 6,306,423 B1 | 10/2001 | Donovan et al. |
| 6,312,706 B1 | 11/2001 | Lai et al. |
| 6,312,708 B1 | 11/2001 | Donovan |
| 6,383,509 B1 | 5/2002 | Donovan et al. |
| 6,429,189 B1 | 8/2002 | Borodic |
| 6,447,787 B1 | 9/2002 | Gassner et al. |
| 6,461,617 B1 | 10/2002 | Shone et al. |
| 6,545,126 B1 | 4/2003 | Johnson et al. |
| 6,573,241 B1 | 6/2003 | Bigalke et al. |
| 6,579,847 B1 | 6/2003 | Unger |
| 6,585,993 B2 | 7/2003 | Donovan et al. |
| 6,620,617 B2 | 9/2003 | Mathiowitz et al. |
| 6,622,051 B1 | 9/2003 | Bishay et al. |
| 7,022,329 B2 | 4/2006 | Donovan |
| 7,140,371 B2 | 11/2006 | Zdanovsky |
| 7,192,596 B2 | 3/2007 | Shone |
| 7,211,261 B1 | 5/2007 | Moyer et al. |
| 7,238,357 B2 | 7/2007 | Barron |
| 7,270,826 B2 | 9/2007 | Borodic |
| 7,288,529 B2 | 10/2007 | Sanders et al. |
| 7,335,367 B2 | 2/2008 | Borodic |
| 7,459,164 B2 | 12/2008 | Borodic |
| 7,491,403 B2 | 2/2009 | Borodic |
| 7,691,394 B2 | 4/2010 | Borodic |
| 7,943,152 B2 | 5/2011 | Borodic |
| 7,964,199 B1 | 6/2011 | Bigalke et al. |
| 8,192,979 B2 | 6/2012 | Borodic et al. |
| 8,241,640 B2 | 8/2012 | Borodic |
| 8,398,998 B2 | 3/2013 | Bigalke et al. |
| 8,580,745 B2 | 11/2013 | Borodic |
| 8,679,486 B2 | 3/2014 | Borodic |
| 9,066,851 B2 | 6/2015 | Borodic |
| 2001/0043930 A1 | 11/2001 | Aoki et al. |
| 2001/0053370 A1 | 12/2001 | Donovan |
| 2002/0006905 A1 | 1/2002 | Aoki et al. |
| 2002/0095158 A1 | 7/2002 | Dixon et al. |
| 2002/0107199 A1 | 8/2002 | Walker |
| 2002/0192239 A1 | 12/2002 | Borodic et al. |
| 2002/0197279 A1 | 12/2002 | Aoki et al. |
| 2003/0036502 A1 | 2/2003 | Gassner et al. |
| 2003/0054975 A1 | 3/2003 | Voet |
| 2003/0059912 A1 | 3/2003 | Bigalke et al. |
| 2003/0086899 A1 | 5/2003 | Jafari |
| 2003/0108597 A1 | 6/2003 | Chancellor et al. |
| 2003/0113349 A1 | 6/2003 | Coleman et al. |
| 2003/0118598 A1 | 6/2003 | Hunt |
| 2003/0135241 A1 | 7/2003 | Leonard et al. |
| 2003/0138437 A1 | 7/2003 | Hunt |
| 2003/0143249 A1 | 7/2003 | Lamb |
| 2003/0166238 A1 | 9/2003 | Shone et al. |
| 2003/0180289 A1 | 9/2003 | Foster et al. |
| 2004/0028703 A1 | 2/2004 | Bigalke et al. |
| 2004/0037853 A1 | 2/2004 | Borodic |
| 2004/0071735 A1 | 4/2004 | Marchini et al. |
| 2004/0082540 A1 | 4/2004 | Hermida Ochoa |
| 2004/0126396 A1 | 7/2004 | Aoki et al. |
| 2004/0151741 A1 * | 8/2004 | Borodic ............ A61K 9/0019 424/239.1 |
| 2004/0175400 A1 | 9/2004 | Borodic |
| 2004/0247606 A1 | 12/2004 | Borodic et al. |
| 2005/0031648 A1 | 2/2005 | Brin et al. |
| 2005/0112146 A1 | 5/2005 | Graham |
| 2005/0119694 A1 | 6/2005 | Jacobs et al. |
| 2005/0142150 A1 | 6/2005 | Graham |
| 2005/0208075 A1 | 9/2005 | Borodic |
| 2005/0208076 A1 | 9/2005 | Hunt |
| 2005/0214326 A1 | 9/2005 | Hunt |
| 2005/0238663 A1 | 10/2005 | Hunt |
| 2005/0238664 A1 | 10/2005 | Hunt |
| 2005/0238667 A1 | 10/2005 | Hunt |
| 2006/0147471 A1 | 7/2006 | Borodic et al. |
| 2006/0269575 A1 | 11/2006 | Hunt |
| 2007/0020294 A1 | 1/2007 | Marchini et al. |
| 2007/0026019 A1 | 2/2007 | Hunt |
| 2007/0129745 A1 | 6/2007 | Suh et al. |
| 2009/0232850 A1 | 9/2009 | Manack et al. |
| 2009/0324647 A1 | 12/2009 | Borodic |
| 2010/0034853 A1 | 2/2010 | Garcia et al. |
| 2011/0104061 A1 | 5/2011 | Seward |
| 2012/0088732 A1 | 4/2012 | Bigalke et al. |
| 2012/0238504 A1 | 9/2012 | Moyer et al. |
| 2014/0315820 A1 | 10/2014 | Borodic |

FOREIGN PATENT DOCUMENTS

| | | |
|---|---|---|
| DE | 19856897 | 6/2000 |
| EP | 0593176 | 4/1994 |
| WO | 94/00481 | 1/1994 |
| WO | 96/39166 | 12/1996 |

(56) References Cited

FOREIGN PATENT DOCUMENTS

| WO | 97/35604 | 10/1997 |
| WO | 99/03483 | 1/1999 |
| WO | 00/15245 | 3/2000 |
| WO | 00/24419 | 5/2000 |
| WO | 200139719 A1 | 12/2000 |
| WO | 01/58472 | 8/2001 |
| WO | 03/041724 | 5/2003 |
| WO | 04/060384 | 7/2004 |
| WO | 2009121632 A1 | 4/2009 |
| WO | 00174703 | 6/2009 |

OTHER PUBLICATIONS

A Kohl, WH, et al. "Comparison of the effect of botulinum toxin A (Botox R) with the highly-purified neurotoxin (NT 201) in extensor digitorum brevis muscle test" Poster Sessions E & F, Wednesday, Jun. 14, 2000, p. 805.

Borodic, Gary et al. "Botulinum Toxin for Aberrant Facial Nerve Regeneration: Double-Blind, Placebo-Controlled Trial Using Subjective Endpoints." Facial Nerve Regeneration, vol. 116, No. 1:36-43, (Jul. 2005).

Borodic et al. "Botulinum toxin therapy, immunologic resistance, and problems with available materials." Neurology 46:26-29, (Jan. 1996).

Johnson, H.M. et al. "The Use of a Water-Soluble Carbodiimide as a Coupling Reagent in the Passive Hemagglutination Test." The Journal of Immunology, vol. 97, No. 6: 791-796, (1966).

Pivalizza et al. "Avoidance of Epidural blood Patch in late Postpartum Eclampsia." J. Clin. Anesth., vol. 11 :615-616, (Nov. 1999).

Schmidt, J. J. et al. "Endoproteinase Activity of Type A Botulinum Neurotoxin, Substrate Requirements and Activation by Serum Albumin." Journal of Protein Chemistry, vol. 16(1 ):19-26, (1997).

Rollnik et al. "Low-Dose Treatment of Cervical Dystonia, Blepharospasm and Facial Hemispasm with Albumin-Diluted Botulinum Toxin Type A Under EMG Guidance." Eur Neurol 2000; 43:9-12.

Goodnough et al. "Stabilization of Botulinum Toxin Type A during Lyophilization." Allied and Environmental Microbiology, Oct. 1992, p. 3426-3428.

Gassner et al. "Addition of an Anesthetic Agent to Enhance the Predictability of the Effects of Botulinum Toxin D Type A Injections: A Randomized Controlled Study." Mayo Clin Proc. Jul. 2000;75(7):701-4.

Epinephrine package insert #58-6165, Abbott Laboratories, pp. 1-5, May 2000.

Langhein et al. "Antibody response to bacterial antigens covalently bound to biodegradable polymerized serum albumin beads." Journal of Applied Bacteriology 1987, 63, 443-448.

International Search Report for PCT No. PCT/1803/06145 dated Aug. 11, 2005. All Pages.

International Search Report and Written Opinion for,PCT/US2006/015459 dated Mar. 1, 2007. All Pages.

Allergan, Inc. Botox® Product Insert, Revised Oct. 2004, 1-4, U.S.A.

Communication pursuant to Article 96(2) EPC for 03 814518.1-2107 dated Sep. 4, 2006.

Xeomin® product information, Merx Pharmacetuicals, LLC, pp. 1-17, see section 11, "Descrption", p. 8 for human serum albumin of 1 mg persent in the composition, and dated 2011.

Botox package insert Allergan Pharmaceuticals, pp. 1-4.

Borodic et al. "Botulinum B Toxin as an Alternative to Botulinum A Toxin, A Histologic study." Ophthalmic Plastic and Reconstructive Surgery 9(3): 182-190 (1993).

Troll et al. "Diplopia after cataract surgery using 4% lidocaine in the absence of Wydase (sodium hyaluronidase)." Journal of Clin Anesth. Nov. 1999; 11(7):615-6.

Borodic et al. "Botulinum A Toxin for Treatment of Aberrant Facial Nerve Regeneration." Plastic and Reconstructive Surger, (91)6: 1042-1045, 1993.

Schantz et al. "Standardized Assay for Clostridium Botulinum Toxins." Journal of the AOAC, vol. 61, No. 1, 1978.

Pearce et al. "The Median Paralysis Unit: A More Pharmacologically Relevant Unit of Biologic Activity for Botulinum Toxin." Toxicon, vol. 33, No. 2, pp. 217-227, 1995.

Carruthers et al, Skin Therapy Letter, vol. 13(6) Jul.-Aug. 2008, Botulinum toxin Products Overview, pp. 1-8.

Borodic. "Botulinum A Toxin for (expressionistic) ptosis overcorrection after frontal is sling." Ophtalmic Plastic & Reconstructive Surg. 8(2): 137-142, (1992).

Borodic et al. "Botulinum A Toxin for the treatment of spasmodic torticollis: Dysphagia and Regional Toxin Spread." Head & Neck, 12:392-398 (1990).

Nussgens et al. "Comparison of two botulinum-toxin preparations in the treatment of essential blepharospasm." Graefes Arch Clin Exp Ophtalmol 235(4): 197-199 (1997).

Bigalke et al. "Botulinum A Toxin: DYSPORT Improvement of biological availability." Exp. Neural. 168(1): 162-170 (2001 ).

Lew et al. "Botulinum toxin type B: a double-blind, placebo-controlled, safety and efficacy study in cervical dystoria." Neurology 49(3): 701-707 (1997).

Borodic et al. "Botulinum Toxin: Clinical and Scientific Aspects." Ophthalmology Clinics of North America 4: 491-503 (1991).

Borodic et al. "Botulinum: a toxin for spasmodic torticollis, multiple vs single point injections per muscle." Head and Neck 14:33-37 (1992).

Ranoux et al. "Respective potencies of DYSPORT and BOTOX: a double blind, randomized, crossover study in cervical dystonia." J. Neuro. Neurosurg. Psychiatry 72:459-462 (2002).

Borodic et al. "Botulinum toxin therapy, immunologic resistance, and problems with available materials." Neurology 996, 46:26-29.

Sesardic et al., Biologicals, vol. 31, 2003, pp. 265-276.

Mclellan et al. "Therapeutic botulinum type A toxin: factors affecting potency." Toxion, col. 34(9), pp. 975-985, 1996.

Dressler et al, "Measuring the ptency labelling of onabotulinumtoxinA (Botox®) and incobotulinumtoxinA (Xeomin®) in an LD50 assay." J Neural Transm. 2012, vol. 119, pp. 13-15.

Borodic et al., "New Concepts in Botulinum Toxin Therapy." Drug Safety 11(3): 145-152, 1994.

Marchetti et al., "Retrospective Evaluation of the Dose of Dysport and BOTX in the Management of Cervical Dystonia and Blepharospasm: The Real Dose Study." Movement Disorders, vol. 20, No. 8, 2005, pp. 937-944.

Giorgio et al. The Lancet, vol. 352, Aug. 22, 1998, pp. 6-25.

O'Day. "Use ofbotulinum toxin in neuro-ophthalmology." 2001, vol. 12(6), pp. 491-22.

Verheyden et al. "Other noncosmetic uses of botox." Seminars in Cutaneous Medicine and Surgery, vol. 20(2), Jun. 2001, pp. 121-126.

Pearce et al. "Review Article: Pharmacologic Characterization of Botulinum Toxin for Basic Science and Medicine." Toxicon, vol. 35, No. 9, pp. 1373-1412, 1997.

Wohlfarth et al., "Pharmacokinetic Properties of Different Formulations of Botulinum Neurotoxin Type A." Movement Disorders, vol. 19, Suppl. 8, 2004, pp. S65-S67.

Foote et al. "Albumin bound and alpha2-macroglobulin bound zinc concentrations in the sera of healthy adults." Journal of Clinical Pathology, vol. 37, Sep. 1984; 37(9):1050-4.

Masuoka et al. "Zinc (II) and Copper (II) Binding to Serum Albumin." The Journal of Biological Chemistry, vol. 269 (41) Oct. 14, pp. 25557-25561, 1994.

* cited by examiner

EXTENDED LENGTH BOTULINUM TOXIN FORMULATION FOR HUMAN OR MAMMALIAN USE

RELATED APPLICATIONS

This application is a divisional application of U.S. patent application Ser. No. 13/132,855, which is a U.S. national stage application of International Application No. PCT/US2009/066891, which claims priority to U.S. provisional application Ser. No. 61/193,513, filed Dec. 4, 2008, the disclosures of which are incorporated by reference herein in their entireties.

FIELD OF THE INVENTION

Botulinum toxin has become a mainstream therapeutic agent for a number of therapeutic cosmetic areas. The therapeutic fields have included movement diseases of the face, blepharospasm, hemifacial spasm, bruxism, temporomandibular joint condition, as well as a number of headache syndromes. Headache syndromes include migraine headache, tension headache, cervicogenic headaches, sinus-related headaches, and postoperative wound pain. Botulinum toxin preparations exist in distinct immunotypes A through G. Each immunotype has distinct amino acid sequences, tertiary structures, axonal cell membrane binding receptors and cytoplasmic substrate. Immunotypes A and B have been conventionally used in the United States. Research preparations consisting of immunotypes C-G are under investigation. In embodiments of the present invention the botulinum neurotoxin comprises any combination or single species of immunotype A-G. In other embodiments, the neurotoxin comprises any combination or single species of immune subtypes A1, A2, or A3.

Because the active botulinum protein is a toxin, low protein loads are needed to achieve biologic effect for pharmaceutical use. These protein exposures are low in therapeutically active forms which allows for repeated injections without inciting an immune response. Occasionally however, repeated injections have been associated with immunologic reactions with the formation of serologic antibodies which can neutralize the effect of botulinum toxin. These antibodies, although occurring at a low frequency, are directly related to the amount of active and inactive neurotoxin. Complex preparations of the botulinum toxin have a molecular weight of 900,000 kD and are formulated with stabilizing proteins, usually human albumin. The specific activity of purified complex is about 30 U/ng. Pure neurotoxin (molecular weight 150,000) is formulated also with human albumin and often has a specific activity in therapeutic preparations of the order of 180-220 U/ng.

Inherent in the treatment of patients with named afflictions is the need for repeated injections. Injections with these agents involve puncturing the skin and placing the toxin into the muscle close to the location of the neuromuscular junctions. Toxin will bind to the pre synaptic axonal membranes within the muscle neuromuscular junctions and effectively block the release of acetylcholine. Receptors binding with neurotoxin occurs with varying affinity but is particularly strong with type A toxin. Diffusion throughout the muscle and adjacent muscles is dependent on the amount of toxin given, binding affinity of the various neurotoxin immunotypes, and stabilizing excipient characteristic and concentrations. Toxin immunotypes with poor binding affinity or preparations formulated with low concentrations of excipient proteins diffuse rapidly away from the injection target are more likely to be less potent, requiring more neurotoxin protein mass to achieve a desired clinical and therapeutic result. In these preparations more units are needed to achieve therapeutic success, sometimes with a decreased duration of action. Sequestration is an important aspect of the botulinum pharmacokinetics as has been outlined in the following applications and patents: (1) U.S. Pat. No. 7,491,403, issued Feb. 17, 2009; (2) U.S. Pat. No. 7,459,164, issued Dec. 2, 2008; (3) U.S. Provisional Application No. 60/383,570, filed May 28, 2002; and (4) U.S. Provisional Application No. 60/435,901, filed Dec. 20, 2002. The disclosures of these four applications and patents are incorporated herein in their entireties by reference thereto.

Greater mass of neurotoxin per injections can result in secondary antibody formation which destroys the longevity of effectiveness.

Because the duration of action is limited to 4 months, repeat therapy needs to be conducted at three to four month intervals for most if not all commonly used indications. This creates opportunity for inconvenience to the patient, need for loss of hours from work, need for repeated punctures in the skin which are painful, and also the potential for more neurotoxin protein dosing exposures which can lead to immunologic reaction and possible permanent loss of therapeutic effects. Botulinum toxins with the longest duration of action would be considered preferable to conventionally used preparations as many of the disadvantages can be mitigated.

SUMMARY OF THE INVENTION

In one embodiment, the invention comprises a pharmaceutical composition comprising a botulinum neurotoxin, an adhesive agent, and a stabilizing macromolecule. The stabilizing macromolecule may be a stabilizing protein. In one embodiment, the stabilizing protein also acts as the adhesive agent. In one embodiment, the stabilizing macromolecule is a stabilizing polysaccharide. In various embodiments, the adhesive agent is a sequentially or simultaneously administered fibrinogen thrombin preparation. In various embodiments, the stabilizing protein comprises an adhesive protein or component of an adhesive protein. The macromolecule or adhesive agent may be freeze or flashed dried. In some embodiments, the botulinum neurotoxin, the adhesive agent, and the stabilizing macromolecule may be in liquid or gel phase. Exemplary non-limiting stabilizing proteins include fibrinogen, thrombin or human serum albumin. These proteins may be recombinantly manufactured. Exemplary non-limiting adhesive agents (bioadhesive agents) include a fibrinogen and an antifibrinolysin, sequentially or simultaneously applied albumin and gluteraldehyde, cyanoacrylate compounds (which may be adsorbable in some embodiments), a lipolytic agent, for example, phosphatidyl, choline, or deoxycholines, or a bile acid. In other embodiments, the adhesive agent comprises a microparticle which causes adhesion of an undersurface of a muscle to facial bones. Exemplary non-limiting microparticles include collagen, polyethylene, and hydroxyappetite.

In one embodiment, the invention includes a syringe and a dual barrel needle capable of delivering the botulinum neurotoxin, the adhesive agent, and the stabilizing macromolecule sequentially or simultaneously. In one embodiment, the botulinum neurotoxin, the adhesive agent, and the stabilizing macromolecule are not premixed, thereby allowing sequential delivery. The botulinum neurotoxin may comprise any combination or single species of immunotype A-G or any combination or single species of immune subtypes A1, A2, or A3. In other embodiments, the neurotoxin may be a chimeric neurotoxin.

In another embodiment, the invention includes a pharmaceutical composition comprising a botulinum neurotoxin, an adhesive agent, a stabilizing sugar, and a stabilizing protein.

In one embodiment, a method of treating involuntary facial movements in a human patient comprising the step of injecting a therapeutically effective amount of embodiments of the above referenced compositions to a human patient, wherein administration of the composition reduces symptoms of involuntary facial movements is disclosed. In other embodiments, methods of cosmetically treating wrinkles, modifying facial contour for functional or cosmetic purposes, methods for: treatment of involuntary movements of the head and neck or limbs, treatment of spasmodic Torticollis, treatment of spasmodic cerebral palsy, treatment of spasticity due to head injury, degenerative neurologic diseases, or stroke, treatment of hyperactive bladder and interstitial cystitis, treatment of prostate hypertrophy and other forms of bladder hyperactivity, treatment of long bone fractures, treatment of scoliosis, treatment of tight neck bands, and treatment of migraine or tension headache are disclosed.

In one embodiment, a method of extending the duration of action of any botulinum toxin based pharmaceutical by combining an agent to the formulation or the administration procedure which causes an adhesion between the undersurface of the facial muscle targeted for injection and underlying bone or periosteal surface is disclosed. In another embodiment, a method of extending a duration of action of a botulinum toxin based pharmaceutical comprising a step of combining an agent with the botulinum toxin; wherein said agent causes an adhesion between the undersurface of a muscle targeted for injection and underlying bone, periosteal surface, myofascial covering, fascial coverings, or tendon surroundings is disclosed. In yet another embodiment, a method of extending the duration of action of any botulinum toxin based pharmaceutical comprising a step of combining an agent with the botulinum toxin; wherein said agent causes intramuscular adhesions between fibers, fiber bundles, and fibers and fascial coverings, thereby decreasing effective contraction by tethering muscles fibers, fiber bundles and muscles coverings is disclosed.

Also disclosed herein are methods to measure the increased duration of action of a botulinum toxin based pharmaceutical. In one embodiment, a method comprising steps of assaying a control prefill of a botulinum toxin based pharmaceutical formulation using a regional denervation activity assay; assaying a control postfill of a botulinum toxin based pharmaceutical formulation combined with one or more stabilizing excipients using a regional denervation activity assay; assaying a test prefill of a botulinum toxin based pharmaceutical formulation comprising a bioadhesive using a regional denervation activity assay; assaying a test postfill of a botulinum toxin based pharmaceutical formulation comprising a bioadhesive combined with one or more stabilizing excipients using a regional denervation activity assay; matching the test postfill with the control postfill based on their respective assays; injecting the control postfill into glabellar muscles; injecting the test postfill into glabellar muscles; objectively measuring the degree of effacement of glabellar rhytides over fixed intervals involving single and multiple injection cycles for both the control and test postfills; and comparing duration of effect at the fixed intervals to determine the extent and duration of effect of the control and test postfills is disclosed. In other embodiments, a method which further comprises assaying using an $LD_{50}$ assay is disclosed. The above methods for measuring the increased duration of action of a botulinum toxin based pharmaceutical may also be done on formulations that do not have stabilizing excipients.

DESCRIPTION OF THE FIGURES

FIG. 1 depicts a sagittal view of the human face transecting the eye. The white configuration under the skin represents fibrofatty tissue. The fibrofatty tissue is seen anterior and posterior to facial muscles and below the eye. The figure illustrates the extent of the pre-periosteal, sub-aponeurotic and sub dermal fat can be seen on the magnetic resonance image of the forehead scalp and skull table. The T1 weighted image demonstrates the high contrast fat layer in the pre-periosteal, sub-aponeurotic region and in the anterior region of the orbicularis frontalis muscle region above the eyebrow. The fat pads in front and behind the muscle (lighting up white in the scan) represent a low resistance "sandwich" by which these facial muscles move without substantial resistance.

DETAILED DESCRIPTION

As used herein, "skin puncture" is a puncture through skin made with a medical needle between 4-32 gauge. In a preferred embodiment, a skin puncture is made with a medical needle between 25-30 gauge.

As used herein, "small incision" or "micro incision" is an incision less than 10 mm. In a preferred embodiment of the present invention, a small incision is less than 3 mm. In another preferred embodiment of the present invention, a small incision is less than 2 mm. In another preferred embodiment of the present invention, a small incision is less than 1 mm.

As used herein, "large incision" is an incision greater than 1 cm.

As used herein, a "method of injection as to avoid nerves, arteries, and veins" refers to anatomic knowledge possessed by the surgeon, which contemplates natural variations of usual and unusual positions of critical nerves and vessels which can be injured by microincisions, implantable devices, or injections of bioadhesives.

The botulinum toxin is stabilized with an adjuvant protein at much higher concentrations than the neurotoxin. Usually this is human serum albumin, although recombinant albumins have been tried in research preparations and have been the subject of prior inventions by the inventor, as described, for example in U.S. Pat. No. 7,459,164, referred to above. Other proteins are known to stabilize the toxin. These include bovine serum albumin, lysozyme, gelatin, casein, hyaluronidase as well as other protein bulking agents. Hyaluronidase is disclosed in, for example, U.S. patent application Ser. No. 12/083,058, filed Aug. 3, 2009, titled "Albumin-Free Botulinum Toxin Based Pharmaceutical Compositions Containing a Hyaluronidase and Methods of Use," the disclosure of which is incorporated herein in its entirety by reference thereto. The bulking agents help to stabilize the toxin during freeze drying as well as may play a role in the sequestration of the material in the highly diluted form. In addition to sequestration, adjuvant proteins have been known to sustain and maintain the integrity of the toxin activities during high dilutions. Critical and optimum concentrations of adjuvant stabilizing proteins are determined by diluting the toxin in different concentrations of adjuvant proteins and determining the concentration of adjuvant protein so the bioactivity is preserved at high dilution. Stabilization during freeze drying can also be useful for qualifying an excipient bulking agent. This qualifying exercise will simulate the in vivo situation in which the injectable formulation will undergo dilution from interstitial fluids surrounding muscular and nerve tissues.

In various embodiments of the invention, the botulinum toxin is stabilized with a stabilizing macromolecule, which may be, for example a stabilizing protein or a stabilizing polysaccharide. In various embodiments, the stabilizing macromolecule and/or the bioadhesive agent(s) may be freeze or flashed dried. In various embodiments, the botulinum neurotoxin, the adhesive agent, and the stabilizing macromolecule are in liquid phase or gel phase.

Other elements of the preparations have included stabilizing monosaccharide, disaccharide, and polysaccharide sugars inclusive of lactose, mannitol, trehalose and sucrose.

Sodium chloride has been placed in some of the preparations; however, these salt environments are not favorable to freeze drying as they can cause an activation of the toxin molecule from hypertonicity during the drying process.

The addition of adjuvant protein, such as albumin, has originally been thought to keep the neurotoxin molecule away from the silicate glass so the toxin did not get deactivated with vessel to vessel transfers. Other proteins are showing to have the same effect.

After repeated injections of botulinum toxin muscles showed integrity without loss of functionality. The botulinum toxin injection into a muscle works to decrease the contractility of the muscle and a dose dependent response. To quantify, the activity units usually used are the $LD_{50}$ for a population of 20 g-30 g mice.

When used for cosmetics, it has been shown that botulinum toxins can provoke an immune response causing loss of activity and loss of ability to reduce contractility in dynamic frown lines on the face as well as other dynamic facial lines. This is a particularly concerning to medical practitioners as botulinum toxin has many therapeutic applications, inclusive of those previously mentioned with additionally its use in stroke for spasticity, after head injuries, in prostate hypertrophy, hyperactive bladder, certain bowel muscle contractility defects. The toxin may even have some anti-inflammatory components to its behavior. The cosmetic patient can eventually become a therapeutic patient, requiring this pharmaceutical for disease treatment.

It is a suitable pharmaceutical goal to try to increase the duration of action of botulinum toxin to enhance convenience, decrease exposure of proteins, and to potentiate the effects of botulinum toxin in its use in the medical practice.

In addition to an enhanced duration of action, another possible quality of an improved botulinum toxin based pharmaceutical would be to cause permanent effects such that withdrawing use of the toxin for extended periods can lead to lasting residual beneficial effects, even after the biologic weakening effects of botulinum toxin have worn off. This has not been the case with the use of multiple botulinum injections of any immunotype over a period of time with multiple dosing exposures. After botulinum toxin has been given over a number of years and the toxin injections are stopped, the muscle will re-assume its configuration to a normal volume and strength without evidence of denervation and without evidence of decreased contractility or any permanent long-term effects.

Design of a Long-Term Botulinum Toxin Formation

Recently the inventor has described a characteristic of the functional anatomic system which helps govern facial muscle contractility and human facial expression and configuration. More specifically, the system of facial muscles is surrounded by a thin plane of fat between the periosteum of flat surfaced facial bones and the undersurface of facial muscles and fat on the anterior superficial surface. The fat plane on top and bottom of the facial muscles are described herein as producing a low resistance environment so the each facial muscle may contract individually or in concert with other facial muscles to create facial expression, as well as facial wrinkling, and other dynamic facial lines as well as facial contour. Facial muscles, such as zygomaticus major and minor, frontalis, orbicularis, mentalis, as well as other facial muscles are specifically attached at places along the flat bones of the face. Flat bone consists of frontal, zygomatic, maxillae, mandible, nasal, and temporal bones. These attachments are called insertions which anchor the facial muscle, allowing the force generated by the contractility of the facial muscles to be delivered to superficial aspects of the face, inclusive of skin and dermis. This force delivery is critical for facial appearance and configuration. The movements and tone generated by facial muscles help create dynamic lines in the face, like transverse forehead wrinkles, nasolabial fold, glabellar lines, as well as dimples and chin lines. These lines are associated with changes in the positions of soft tissues and contours of the face and generate the psychodynamic of facial expression (sad appearance, happy appearance, stern appearance, angry appearance etc.). Facial muscle tone also influences contour, such as malar eminence location, jowl position, brow position, and lip position. Facial expression is critical to a normal social human existence as it is the major method of non-verbal communication between human beings revealing mood and affect individual feelings. The movement of facial muscles is a function of contractility of the muscle, its attachments to its origin, which are the facial bones, and its insertions in the undersurface of the dermis. The muscles are located in a fibrofatty fascia called the SMAS (superficial muscle aponeurotic system). The SMAS is considered a reticular network in which the facial muscles are suspended and influence different configuration changes of the contour of the face during active expression as well as at rest. It is typically this layer that the facial plastic surgeon institutes a jowl lifting facelift. This layer is continuous to virtually all facial muscles, including the platysma, which is a superficial muscle of the neck.

Figure 1:
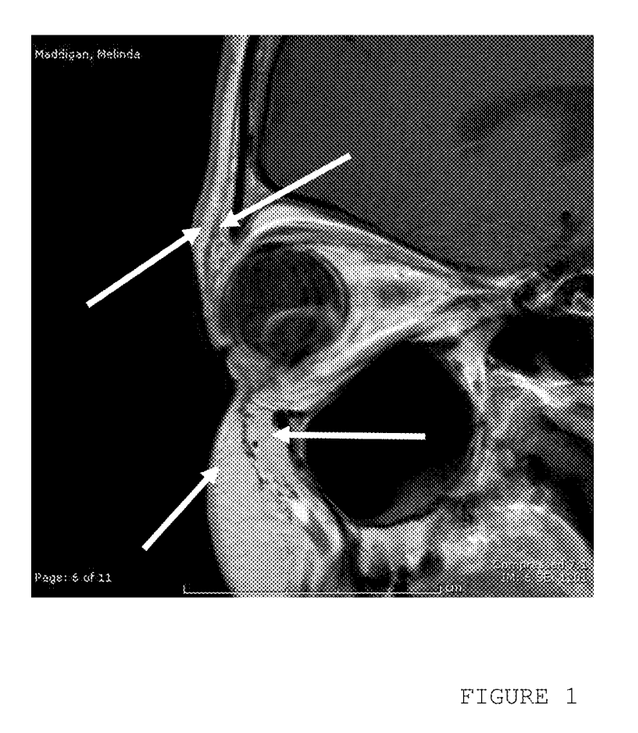

Aside from attachment at the bony plane and integration within the SMAS, an important limiting factor to facial movement is the actual contractile movement of the muscles transmitting the force to the superficial aspects of the face and superficial fat sector which change contour. This requires that the muscles have free movement without mechanical resistance or tethering within the facial layers. Facilitating this free movement of facial muscles are two important fatty layers. The first is the submuscular fibrofatty tissues in front of the periosteum and the second is the fibrofatty tissues on the front (anterior) surfaces of the muscles. This is seen in FIG. 1 for the frontal muscle with arrows pointing to both anterior and posterior portions of these thin fat pads. The thin fat pads work at essentially a low resistance grease-like lubricated planes by which the facial muscles, the SMAS, and attached dermis-skin can move. Alterations in the configuration of these fat pads can influence the motility of the human face. By virtue of altering motility of the face, one can alter the transmission of force to the skin surface, which alters the degree and intensity of facial wrinkles as well as the dynamic of facial contour during active facial expression. The concept of age is related to the degree of embossment of naturally occurring facial wrinkles, such as the nasolabial fold, glabellar lines, crowfeet lines and forehead lines of the face and head. Alterations in contractility of these muscles can decrease these wrinkles as has been shown worldwide by the massive use of botulinum toxin as cosmetics and face altering pharmaceuticals. These lines are essentially the result of decrease in the tensile strength and increased laxity of the dermis associated with aging. Reducing contractility camouflages these lines and produces a more smooth youthful looking face, a quality appreciated by many individuals. This smooth quality is particularly true during facial expression, and with the face in a neutral "at rest" position.

Figure 2:
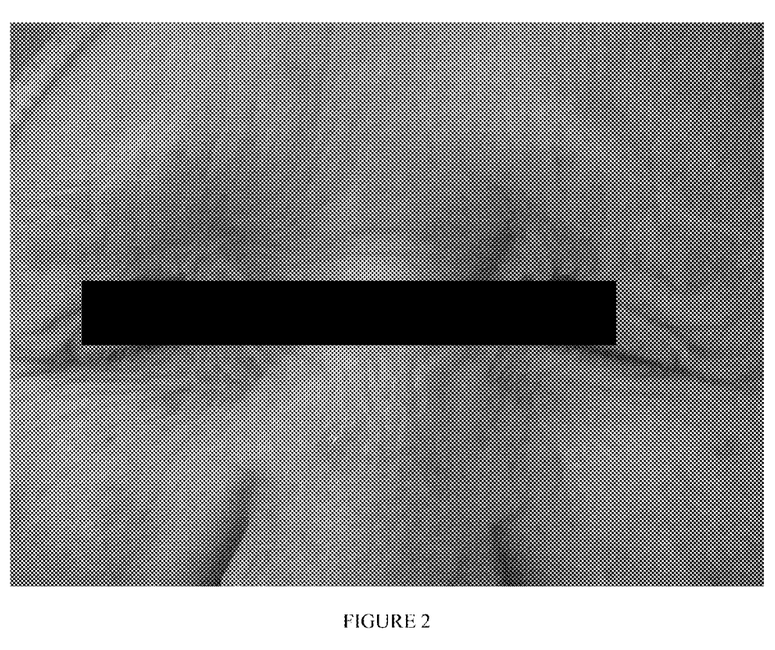
FIG. 2 and FIG. 3 depict placement of small titanium bolting to decrease contractility of facial muscles, such as the orbicularis oculi.
Figure 3:
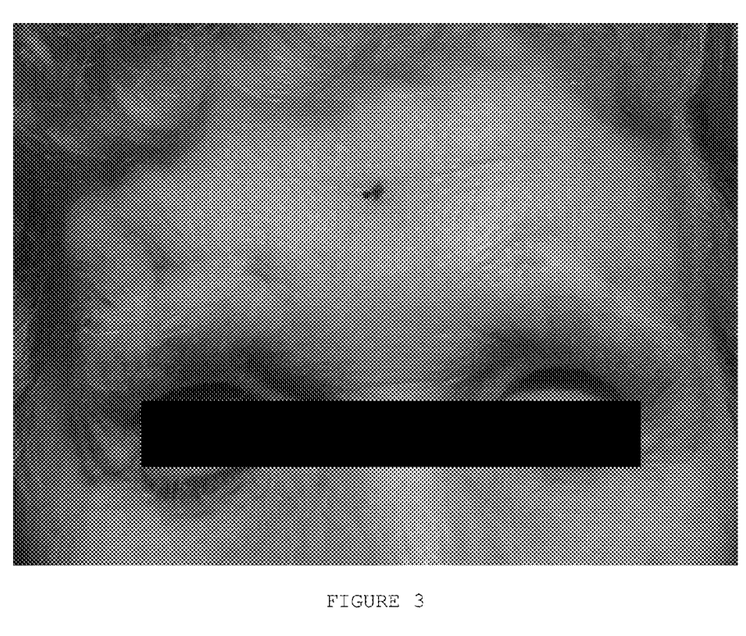

It has recently been shown by the inventor that the placement of small titanium bolting can decrease the contractility of facial muscles, such as the orbicularis oculi. By pinning the muscle to the bone with small 1.3, 1.0 mm or smaller self drilling screws, these muscles can be made to have decreased contractility. Reference is made to FIGS. 2 and 3. In FIG. 2, Maximal orbicular contraction is demonstrated by brow depression with extensive glabellar and peri-ocular wrinkles Note the reduction in contractility of the muscle and smooth of the dynamically induced peri-ocular wrinkles as shown in FIG. 3 after mechanical integration of undersurface of the orbicularis to its underlying bone. After these screws are removed, the decreased contractility seems to be maintained because of adhesions created on the undersurface of the facial muscles within the fibrofatty layer between facial muscles and bone and its periosteum. The fibro fatty layer essentially becomes fibrotic and tethers the muscle to the flat facial bones. By virtue of doing this, contractility of the muscle is reduced and the wrinkle dynamic and static wrinkles of the face are also reduced. The pins can be maintained and removed after a period of time resulting in a sustained effect on the contractility of the facial muscle.

The concept of the influence of fibro fatty layers on the facial muscle contraction and tone an opportunity for an extended length botulinum toxin preparation. The botulinum toxin preparations are currently injected into the muscle, allowed to diffuse into a certain area, binds and is internalized at axonal neuronal receptors and acts on cytoplasmic substrates syntaxin, SNAP-25 and VAMP. Positioning the injections is important in order to produce the precise effects on specific muscles, muscle groups, or components of individual muscles. After several months, the chemical effects on altered contractility disappear. The invention described herein involves using a combination of botulinum toxin composition which will by mechanism:

1. effectively have all the properties to cause chemodenervation through a facial muscle that virtually all predecessor botulinum toxin preparations have had; and
2. agents which create a fibrotic adhesion on the under surface of facial muscles to the facial bone so that the facial bone tethers the under surface of the facial muscle (causing fibrosis to the underlying fat pad).

This is to be accomplished by two methods. First, altered placement of the botulinum toxin under the muscle rather than into the muscle. Diffusion should still be possible of the neurotoxin molecule to the muscle as facial nerves enter each facial muscle from its under surface, arborize, and formulate the myoneural junctions close to the under surface of the muscles. Secondly, the excipient stabilizing protein will promote a reaction by which the muscle essentially scars to the underlying flat facial bone. Alternatively, a preparation which specifically works only by the second mechanism can be employed.

A non-limiting example of the formulation described herein includes:
1) a botulinum toxin neurotoxin,
2) a stabilizing protein which comprises fibrinogen or thrombin,
3) a dual barrel injection needle or sequential injection system which delivers the pharmaceutical liquid or powder
4) a thrombin mediated conversion of fibrinogen to fibrin, and subsequent bloodless clot formation, which provokes inflammatory mediators.

In any of the embodiments of the present invention, the botulinum toxin neurotoxin may be chimeric.

A more generalized non-limiting formulation described herein using the same mechanism as above includes:
(1) A botulinum toxin neurotoxin;
(2) stabilizing macromolecule (for example but not limited to a protein or polysaccharide); and
(3) a bioadhesive within the vial capable of producing tethering of the undersurface of a facial muscle without deactivating the biologic properties of the neurotoxin.

The bioadhesive may include a variety of chemical agents designed to produce a tethering and restriction of the undersurface of a facial muscle (or other muscle) to bone. Experimentation with $LD_{50}$ determination based a addition of each bioadhesive is the method to determine inert effect on neurotoxin or possible deactivation. One $LD_{50}$ unit is equal to that quantity of botulinum toxin causing a lethal effect in 50% of a population of 20-30 g white mice as described in the standard Schantz-Kauter bioassay using Swiss Webster mice. Described formulations may exist in syringes, vials, or delivery systems which engage delivery concomitantly with neurotoxin injection into a patient.

Bioadhesives or Glues Applicable for Submuscular and Intramuscular Injection which May be Incorporated into a Vial or Dose Container or Integrated into a Delivery Device The following represent non-limiting exemplary bioadhesive or glue types which can be used in various embodiments as an injectable to achieve myo-oseous fixation to control contour changes, wrinkle pattern reduction, and/or elevation of the human face via injection and provide a dual mechanism formulation for migrating facial tone and movement. These agents are qualified by adhesive properties, inflammatory response and duration of adhesion. Although variations are possible based on dose and position, the overriding principle of myo-oseous fixation can be accomplished by one or more of these agents, at varying doses dependent on strength of adhesion, inflammatory complications and duration of effect. Other qualifying parameters include coloration quality with clear or lighter cured glue color being preferable, flow characteristic via delivery device, curing rate (hardening rate), viscosity, and cohesiveness to prevent migration or possible embolic complications. Bioadhesives or glue may be administered in conjunction with botulinum toxin to the undersurface of the facial muscles only if botulinum toxin activity is not substantially destroyed. External devices such as temporary bandages, masks, or tapes can also be used to assist in this minimally invasive procedure.

Fibrin-Thrombin-Fibrinogen

This bioadhesive glue type consists of a dual delivery system which involves the injection of fibrinogen followed by thrombin which catalyzes the conversion of fibrinogen to monomers which cross link to form the fibrin clot. In one embodiment, fibrinogen may be formulated in higher concentrations than human plasma. In various embodiments, fibrinogen can be derived from pooled plasma or from recombinant origins. In other embodiments, thrombin can also be derived from pooled human blood products or from recombinant manufacturing technology. In some embodiments, plasminogen may be removed from such products, as this agent when activated may causes fibrinolysis which degrades the clot and seal properties. Alternatively, agents which inhibit plasmin, for example antiplasmin or antifibrinolysin which can further limit clot degradation. One such inhibitor is aprotinin which is used in the commercial product Tisseel™. Recombinant blood based products limit potential contamination with hepatitis B, C and HIV as well as prion based disease.

In some implementations, glue delivery may be employed in multiple locations and/or given serially to help to further achieve a lasting seal and bioadhesion.

Fibrin based sealants have the potential to induce growth factor for fibrocytes which can enhance sealing capability over time. These materials can control bleeding which can be beneficial when injected into a vascularized muscle.

Commercially available products include Tisseel™, Evicel, Vitage, and Cryoseal.

Thrombin

In some embodiments, thrombin may be used individually as a bioadhesive glue and binding agent. Thrombin may be used in its recombinant form or native form from human or animal based donors. In some embodiments, this agent may be optionally used with gelatin.

Polyethylene Glycol Based Sealants and Bioadhesive Glue

Commercially available non-limiting agents in this class of bioadhesives include Duraseal™ and CoSeal™. In some embodiments, these agents can be used to control bleeding and have sealant and binding capability which may be adapted to muscle bone fixation. Durseal™ is commonly used in the head for outer brain covering procedures.

Gluteraldehyde-Albumin Bioadhesive Sealants

These sealants comprise purified albumin with gluteraldehyde, which when mixed forms a covalent bond between the matrix and cell surfaces. BioGlue™ is a non-limiting example. In one embodiment, removal of gluteraldehyde may be accomplished or, optionally, the gluteraldehyde may remain so long as toxin biologic activity is substantially maintained.

Cyanoacrylate Based Bioadhesive Sealants

Non-limiting examples are 2-octyl cyanoacrylate, N-butyl 2 cyanoacrylate, and absorbable cyanoacrylates, known under the trademark OMNEX™. These agents can effectively stop bleeding. Binding strength is better than fibrin based sealants. In some embodiments, low volume of agent can be effective. Inflammatory potential can potentially enhance long term nature of seal when place under a thin facial muscle. Absorbable cyanoacrylates such as OMNEX may be preferred in some implementations based on reversibility and lack of long term potential for scarring and foreign body reactions. The use of cyanoacrylate is described in more detail below.

Other Types of Bioadhesives

In other embodiments, plasma polymerized N-isopropyl acrylamide (pNIPAM) or ONYX™ are suitable bioadhesives for the present invention.

Use of Cyanoacrylate Derived Bioadhesive Glues as an Injectable Agent for the Purpose of Altering Myo-Osseous Fixation Cyanoacrylate glues are well known adhesives which are known to produce strong bonding during polymerization and form tight bonding with a degree of heat release. Medical applications have commonly included skin approximation as an alternative to conventional sutures for which the material is currently commercialized. Deep tissue implantation has also been advocated for neural trunk repair during soft tissue surgery, vascular repair, fixation of extraocular muscles to the ocular globe, or implanted prosthesis after globe removal, and embolization for vascular malformation using neuroradiologic techniques.

Major concerns from regulators have included excessive inflammatory reactions from chemical breakdown of implanted glue which can form formaldehyde, a chemical toxic to tissues. Heat generation during polymerization and hardening has also been noted but represents a lesser problem. Efforts have been made to find a cyanoacrylate derivative which has a reduced rate of formaldehyde generation. Non-limiting examples of cyanoacrylates suitable for use with the present invention include: alkyl 2-cyanoacrylate, alkenyl 2-cyanoacrylate, alkoxyalkyl 2-cyanoacrylate, and carbalkoxyalkyl 2-cyanoacrylate. The alkyl group may have 1 to 16 carbon atoms and is preferably a C1-C8 alkyl 2-cyanoacrylate. Suitable cyanoacrylates include, for example, methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate, methyl .alpha.-cyanoacrylate, ethyl .alpha.-cyanoacrylate, propyl .alpha.-cyanoacrylate, butyl .alpha.-cyanoacrylate, and cyclohexyl .alpha.-cyanoacrylate, alkenyl and cycloalkenyl .alpha.-cyanoacrylates such as allyl .alpha.-cyanoacrylate, methallyl .alpha.-cyanoacrylate, and cyclohexenyl .alpha.-cyanoacrylate, alkynyl .alpha.-cyanoacrylates such as propargyl .alpha.-cyanoacrylate, aryl .alpha.-cyanoacrylates such as phenyl .alpha.-cyanoacrylate and toluyl .alpha.-cyanoacrylate, hetero atom-containing methoxyethyl .alpha.-cyanoacrylate, ethoxyethyl .alpha.-cyanoacrylate, furfuryl .alpha.-cyanoacrylate, silicon atom-containing trimethylsilylmethyl .alpha.-cyanoacrylate, trimethylsilylethyl .alpha.-cyanoacrylate, trimethylsilylpropyl .alpha.-cyanoacrylate and dimethylvinylsilylmethyl .alpha.-cyanoacrylate.

A preferred cyanoacrylate is 2-octyly cyanoacrylate because of its slow degradation and reduced rate of formaldehyde generation.

In some embodiments the bioadhesive has a slow degradation and reduced rate of formaldehyde generation.

In some embodiments, multiple forms of delivery devices may be used to inject adhesives through a puncture site for the purpose of glue placement in the defined fibro fatty plane on the undersurface of the muscle tissue. Non-limiting delivery devices include: (1) prefilled syringes with sterilized liquid bioadhesive which remain airtight until the moment preceding use; (2) tube enveloping containers capable of delivering a fixed volume of liquid bioadhesive; (3) or diaphragm-shaped containers containing a fixed amount of glue. Any container forms mentioned are not limiting as multiple devices are possible so long as the device maintains sterility of the injectable and is able to deliver a substantially fixed and substantially consistent volume of bioadhesive agent.

Absorbable-Type Cyanoacrylates

A class of cyanoacrylate glues characterized as "absorbable tissue glue" has been advanced and advocated. A limiting factor of cyanoacrylate glues is granuloma formation from breakdown into toxic subcomponents such as formaldehyde. In some embodiments, glues designed to absorb with reduced chance of foreign body inflammatory reaction may be employed. These have a reduced chance to induce this form of complication and have improved tolerability. In preferred embodiments, the cyanoacrylate or an injection amount thereof is selected on the basis of its inflammatory response in patients. In certain embodiments, the inflammatory response is less than about 5% of patients, preferably less than about 2% of patients, and most preferably less than about 0.5% of patients. As used herein, the inflammatory response refers to an unacceptable level of granuloma formation. Although the mechanical adhesion may be temporary, adjuctive inflammatory reaction from single or multiple injections can induce fibrosis which can function as an endogenous glue and adhesive achieving substantially the same effect as a foreign substance. The net effect would be to create a more permanent or lasting adhesion. The tolerability of absorbable cyanoacrylates may, in some embodiments, result in less secondary inflammatory complications, less scarring, and an improved side effect profile than some of the other preparations and agents listed above. Currently, Omnex™ from Johnson and Johnson represents a non-limiting example of the absorbable cyanoacrylate class appropriate for the practice described herein. Absorbable class glues are not to be limited by one formulation or brand as other forms of absorbable bioadhesives can be used to achieve substantially similar results.

Alternatives to Cyanoacrylate-Derived Bioadhesive Glues

Because of the relatively high degree of tissue reactivity induced by some implanted cyanoacrylates, alternative forms of liquid or gel bioadhesives can be applied for the same purpose in some embodiments. These agents may be delivered, for example, by syringe and puncture site. Alternative materials may include various forms of silicone, acrylic, or any other substance demonstrated to have less than 5% induced inflammatory rate which can be combined in a botulinum toxin formulation or botulinum toxin delivery system.

Method of Tissue Manipulation after Injection of the Liquid Bioadhesive-Botulinum Toxin Formulation In some embodiments, after the clinician injects the liquid adhesive he may manipulate the soft tissue overlying the bony surface over which the injection has been administered. This manipulation will alter contour and suspension into a desirable configuration. For example, the method of application using a liquid adhesive would be organized in the following steps:

(1) A small amount of anesthetic (for example but not limited to lidociane) is injected over the desired bony surface within the low resistance fibro fatty tissue plane;

(2) Injection of the liquid bioadhesive agent (for example but not limited to cyanoacrylate bioadhesive glue) over the bone in the fibrofatty plane on the undersurface of the muscle. In one embodiment this step can occur through a puncture site which does not involve an "incision." In another embodiment, this step can occur through a "microincision" these embodiments, hardening and polymerization is initiated. Care is taken to avoid direct injection into nerve, arteries veins, or other anatomically sensitive areas so as to avoid complications;

(3) External tissue manipulation by the clinician so that the soft tissue can be repositioned or re-suspended into a desirable configuration. For instance, frontal bone injection can be followed by manual elevation of the brow to achieve a brow lift. Maxillary and zygomatic bone injections can be administered so as to achieve midface lift by manually elevating the check from the surface over the maxillae and zygomatic bones. Mandibular inferior border, anterior or posterior surface can be injected followed by manipulation of the soft tissue of the jowl region so as to re-suspend and tighten the jowl region, thereby reshaping the jowl to a more contoured and youthful configuration without the use of conventional incisional plastic surgery of the face; and/or optionally (4) Other injection locations in non-facial areas of the body.

The concept and techniques described are above not necessarily be limited by exact anatomic relationships.

Amount of Injectable Glues and Bioadhesives

In some embodiments, the amount of glue or bioadhesives used may be limited by the critical amount which will cause inflammatory, granulomatous reactions or cause excessive tissue contractions with dimpling of the skin surface. In one embodiment, the amount may vary from between about 0.001 mL to about 10 mL per injection site. In other embodiments, the amounts may vary (all given on a per injection site basis) from between about 0.001 ml to about 8 mL, from between about 0.001 mL to about 6 mL, from between about 0.001 mL to about 4 mL, from between about 0.001 mL to about 2 mL, from between about 0.001 mL to about 1 mL, and from between about 0.001 mL to about 0.5 mL. In a preferred embodiment, the amount per injection site is between about 0.1 mL to about 0.2 mL. In some embodiments, multiple injections may be employed depending on the targeted region and strength of adhesion sought per given anatomic region. In some embodiments, multiple injection points per region may be employed.

Injection Devices

In one embodiment, a device comprises a single-use device comprising a needle or micropuncture device, with a bioadhesive, for example but not limited to, cyanoacrylate glue. Other forms of bioadhesives or tissue glues such as thrombin fibrinogen may involve compound needle bores with individual ports corresponding to a given component of the glue or bioadhesive agent needed for curing. In a preferred embodiment of a delivery system, a syringe with a predetermined injection needle or a micropuncture device may be employed to effect single puncture per syringe use. Alternatively, in other embodiments, a multiple use delivery syringe may be used for more rapid administration techniques. In another embodiment, a device which sequentially injects bioadhesive glue followed by botulinum neurotoxin or botulinum neurotoxin followed by bioadhesive glue may be used. The latter embodiment is particularly attractive if the agents are unstable or adversely affect botulinum toxin activity when mixed.

The Effect of the Thrombin Induced Fibrin Clot on Botulinum Neurotoxin Sequestration During this active injection process of thrombin catalyzed fibrinogen to fibrin, a number of clotting factors are activated which stimulates a small degree of inflammation around where there is essentially a blood-free clot. The clot serves to further stabilize the botulinum toxin as well as to promote fibrosis within the fibrofatty layer and ultimately result in the tethering and adhering of the under surface of the muscle to the facial bone, requiring single or serial injections. The muscle loses its contractility after one or more injections by virtue of becoming tethered to the bone, altering contractility of facial muscles, and inciting adhesion in the superficial or preferably deep fibrofatty layer which increased the mechanical resistance to facial muscle contractility.

The combination serves two functions: as a chemodenervating agent and as a tissue bioadhesive glue agent. The fibrin clot forms a matrix for the neurotoxin to adhere and sequester while in close proximity to the neuromuscular junctions anatomically concentrated on the undersurface of, for example, the facial muscles. Additionally, the fibrin clot forms a tethering and eventual fibrosis causes restriction of the facial muscle to movement. In other embodiments, this is equally applicable to other body muscles besides facial muscles. Additionally, glue within the formulation can form a scaffold, that is, a synthetic connective tissue matrix which can restrict contractility of a muscle by tethering fiber to fiber, fiber bundle to fiber bundle, and fiber bundles to surrounding low resistance elements within fatty planes enveloping muscles. The latter mechanism does not directly require muscle to bone adhesion. Any mentioned or unmentioned bioadhesive may be used to accomplish this form of tethering. In preferred embodiments, the bioadhesives employed induce inflammatory reactions in less than 5% of subjects, most preferably in less than 0.5% of subjects.

The practice of this embodiment of the invention, the fibrinogen and thrombin sources can include a recombinant source of either thrombin or fibrinogen, autogenous thrombin or fibrinogen manufactured from the specific individual treated, or thrombin and fibrinogen from pooled blood specimens which have been appropriately tested for pathological viruses and bacteria and screened for prions. Any of these sources should result in a fibrinogen which is converted to fibrin by thrombin, which is not impaired by the presence of minute amounts of botulinum neurotoxins. For embodiments employing albumin based bioadhesive glues, recombinant albumin can be used.

Other forms of adhesive and fibrotic stimulating agents may be used in such formulations. These could include, but are limited to, bovine albumin activated by glutaraldehyde or the use of simultaneous microscopic bolts, for example but not limited to titanium bolts, placed just around the time of administration of botulinum toxin either before or after injection. These procedures can further cause adherence of the muscle to the bone. In some embodiments, micro particles which become integrated by fibrovascular tissues such as hyroxyappetite, polyethylene, collagen microparticles, and other porous synthetics can be used to achieve the adhesions in addition to the chemodenervating effects of botulinum neurotoxins. Other materials which may be used include but are not limited to Dexon™ (polylactic acid); Caprolactone; catgut; polydioxanone (PDS) or other materials prepared from polyester.

Use of botulinum toxin can also be associated with physical techniques to achieve undersurface fixation to flat facial bones. These may include ultrasonic treatment to produce small amounts of lipolysis and inflammation, thermal cautery and radiofrequency used for the sole purpose of creating muscle undersurface adhesion for the purpose of increasing the duration of action of botulinum toxin on facial muscle tone and contractility, microwave frequency altered to heat the hyroxappetite crystal within bone while spearing overlying soft tissue, cuffed thermal radiofrequency needles which heat fat followed by cooling and injection with neurotoxin, laser energy, mechanical bone and periosteal abrasion for the purpose of creating adhesion followed by injection of botulinum neurotoxin, and implantation of absorbable suture over the perioesteum for the sole purpose of inciting an inflammatory response followed by injection of botulinum toxin. Adhesion may alternatively be produced by liposuction or microliposuction in deep fat planes for the purpose of causing adhesion of facial or other muscle to bone.

Use of Lipolytic Agents in Botulinum Toxin Formulation to Increase Adhesion Resistance to Injected Muscles As mechanical resistance plays an import role in muscle contractility, and resistance is determined by quality and degree fat surrounding targeted muscle, reducing fat quantity and fibrosis can be accomplished by lipolytic agents which have been previously used for the purpose of dissolving regional fat by direct injection and altering contour. The application of the lipolysis in this specification would superficially be to dissolve fat surrounding a muscle, causing a minimal degree of inflammatory reaction by a detergent effect on fat cell membranes, shrink the fat and cause fibrosis. Agents capable of accomplishing this effect are phosphatidyl choline (known as Lipostabil™ from Aventis) often used with varying concentration of bile acid emulsifiers for example phoshatidyl, choline, deoxycholines at a concentration between 0.001% and 25% are recommended. In some embodiments, these components can occur in a simple formulation with the neurotoxin or, alternately, be separately delivered in sequence or as a part of a duo syringe system.

Adhesion and Fibrosis Causing Permanent or Lasting Effects

Because the adhesion created according to embodiments of the present invention are within muscle to muscle, muscle to bone, or muscle to fat, the decreased effective contractility of muscle can be more permanent than the standard denervation cycle created by neurotoxin. This allows for a longer duration and a lasting durable effect on injected areas. Additionally, sequestration of toxin molecules within the glue matrix can influence the diffusion rate from the injected region by binding neurotoxin molecules or sequestering the toxin molecules within the injected region.

Definition and Method of Determining an Extended Length Formulation

Botulinum toxin pharmaceuticals are utilized for a number of indications, including, for example: spasticity, blepharospasm, cosmetic rhytides, hemifacial spasm, bruxism, jaw dystonia, achalasia, prostate hypertrophy, bladder and intestinal spasms, cervical dystonia, tremors of face, head, hands, focal dystonias, myofascial headaches, migraine, muscle cramps as well as many other indications which involve an abnormality of muscle tone or movement. Therefore, increasing the duration of action of the muscular effects of the neurotoxins on tone or contractility improves the technology by making the therapy less frequent for those with these afflictions. As injections are often uncomfortable and even at times painful, a longer duration of effect preparation would mitigate the discomfort associated with the administration of the technology and botulinum based pharmaceutical.

An ideal application to statistically prove the extended duration offered by the present invention is the rhytide indication. The measurement of this effect is most consistent, easy to accomplish objectively, and not influenced by disease moment to moment variation associated with many other conditions. In summary, this indication is characterized by less deviation in response, and hence is ideal for measuring duration of action.

The direct method to determined increased duration of action over an existing botulinum toxin preparation would be a side to side, direct comparison study using the glabellar rhytide (frown line) as an applicable endpoint. A formulation according to any of the embodiments of the present invention would be used, containing the equivalent amount of botulinum toxin activity based on $LD_{50}$ analysis as defined in all applicable literature. $LD_{50}$ and denervative response have been shown to be inconsistent with available products to achieve a desired effect. For example, in the treatment of torticollis, 10,000 $LD_{50}$ units of Myoboloc are approximately equivalent to 200 units of BOTOX and approximately 500-1000 units of Dysport. The same is true for other conditions. Therefore, a tighter control of measured biologic activity is needed. This added measure would be regional denervation assays. Such assays allow for normalization of regional denervation among preparations so that normalization of the activity can be tested. Such normalization of biologic activity would be important in determining the effect of an added excipient which produces another mechanism of action in weakening and restricting muscular activity. The container prefill (containing stabilized neurotoxin) and postfill containing stabilized neurotoxin with added excipient would be tested using $LD_{50}$, and/or regional denervation assays such as mouse hindlind, mouse paralysis unit determination, or any other regional determination assay. The comparison is important as to be sure that extent of denervation in not negatively influence by the second excipient, via neurotoxin protein degradation, or possibly other mechanisms. As used herein "matching" means, in one embodiment, comparing approximately equivalent regional denervation activities or $LD_{50}$ activities. This matching will allow for a more meaningful comparison between various formulations such that statistical conclusions may be made. Particularly important is the determination of regional denervation assay in the prefill and $LD_{50}$ so that the prefill is determined to be equivalent prior to mixing the second mechanism excipient. In one embodiment, potency of the neurotoxin could be enhanced by the second excipient, via sequestration of the neurotoxin molecules so that cell surface receptors can be saturated using least amount of toxin with limited diffusion effect. However, as one purpose of the second excipient is to produce an alternate mechanism of weakening, the second excipient should have no substantial adverse reaction with botulinum neurotoxin. In one embodiment described herein, the second excipient is a tissue bioadhesive which tethers muscle and restricts contractility by adherence of muscle fiber to bone and other surrounding tissues.

Glabellar rhytide determination during forced frown and with face at rest would be measured over defined intervals so the intensity of effect can be measured along with duration of effect. The degree of rhytide mitigation is quantitated with a stepped scale, using reference photographs showing a spectrum of rhytide intensities, and matching the degree of rhytides to these standard references. Stepped scales may also involve general descriptions of each step based on intensity and severity of rhytide. Applicable control populations may also be employed, for quantitative determination against controls. In one embodiment of this method, the new botulinum toxin formulation would contain a mixture of the bioadhesive, suitably stabilized in excipients, and existing neurotoxin, also stabilized in suitable excipients, will be the comparative group. Applicable statistics are applied to study designs suitability stratified to protect group characteristic equivalency to provide data to make scientific analysis establishing duration of effect. Duration of effect may be measured over one or more cycles of drugs administration for assessment of additive effect upon repeat injections.

The invention claimed is:

1. A pharmaceutical composition comprising:
    (a) a botulinum toxin; and
    (b) an adhesive agent;
    wherein the adhesive agent comprises a fibrinogen and an antifibrinolysin.

2. The pharmaceutical composition of claim 1, wherein the adhesive agent further comprises sequentially or simultaneously applied albumin and glutaraldehyde.

3. The pharmaceutical composition of claim 1, wherein the adhesive agent further comprises one or more cyanoacrylate compounds.

4. The pharmaceutical composition of claim 1, wherein the adhesive agent further comprises collagen, a lipolytic agent or a bile acid.

5. The pharmaceutical composition of claim 4, wherein the lipolytic agent comprises phosphatidylcholine or one or more deoxycholines.

6. The pharmaceutical composition of claim 1, further comprising a stabilizing macromolecule selected from the group consisting of a stabilizing protein or a stabilizing sugar.

7. The pharmaceutical composition of claim 6, wherein said stabilizing macromolecule comprises both the stabilizing protein and the stabilizing sugar.

8. The pharmaceutical composition of claim 7, wherein the stabilizing sugar is selected from the group consisting of one or more of lactose, mannitol, trehalose and sucrose.

9. The pharmaceutical composition of claim 6, wherein said stabilizing macromolecule comprises the stabilizing protein selected from the group consisting of one or more of fibrinogen, thrombin, and human serum albumin.

10. The pharmaceutical composition of claim 9, wherein the stabilizing protein is fibrinogen.

11. The pharmaceutical composition of claim 10, wherein the fibrinogen is recombinant fibrinogen.

12. The pharmaceutical composition of claim 9, wherein the stabilizing protein is thrombin.

13. The pharmaceutical composition of claim 12, wherein the thrombin is recombinant thrombin.

14. The pharmaceutical composition of claim 6, wherein the stabilizing macromolecule or adhesive agent is freeze or flash dried.

15. The pharmaceutical composition of claim 6, wherein the botulinum toxin, the adhesive agent, and the stabilizing macromolecule are in a liquid phase.

16. The pharmaceutical composition of claim 6, wherein the adhesive agent further comprises a microparticle to cause adhesion of an undersurface of a muscle to bone.

17. The pharmaceutical composition of claim 6, wherein the botulinum toxin is one or more immune subtypes selected from the group consisting of immune subtypes A1, A2, or A3.

* * * * *